(12) United States Patent
Lithwick Yanai et al.

(10) Patent No.: US 9,914,972 B2
(45) Date of Patent: Mar. 13, 2018

(54) METHODS FOR LUNG CANCER CLASSIFICATION

(75) Inventors: Gila Lithwick Yanai, Modin (IL); Hila Benjamin, Rehovot (IL)

(73) Assignee: ROSETTA GENOMICS LTD., Rehovot (IL)

( * ) Notice: Subject to any disclaimer, the term of this patent is extended or adjusted under 35 U.S.C. 154(b) by 683 days.

(21) Appl. No.: 14/008,276

(22) PCT Filed: Mar. 26, 2012

(86) PCT No.: PCT/IL2012/000131
§ 371 (c)(1),
(2), (4) Date: Mar. 17, 2014

(87) PCT Pub. No.: WO2012/131670
PCT Pub. Date: Oct. 4, 2012

(65) Prior Publication Data
US 2014/0309123 A1    Oct. 16, 2014

Related U.S. Application Data

(60) Provisional application No. 61/468,077, filed on Mar. 28, 2011.

(51) Int. Cl.
*C12Q 1/68* (2018.01)
(52) U.S. Cl.
CPC ..... *C12Q 1/6886* (2013.01); *C12Q 2600/158* (2013.01); *C12Q 2600/178* (2013.01)
(58) Field of Classification Search
None
See application file for complete search history.

(56) References Cited

U.S. PATENT DOCUMENTS

| | | | | |
|---|---|---|---|---|
| 5,541,308 | A * | 7/1996 | Hogan | C12Q 1/6811 435/6.12 |
| 2005/0227934 | A1 | 10/2005 | Stoffel et al. | |
| 2007/0264644 | A1 | 11/2007 | Showe et al. | |
| 2007/0299030 | A1 | 12/2007 | Dmitrovsky et al. | |
| 2008/0306017 | A1 | 12/2008 | Croce et al. | |
| 2009/0275039 | A1 * | 11/2009 | Moser | C12Q 1/6844 435/6.12 |
| 2011/0312530 | A1 | 12/2011 | Aharonov et al. | |

FOREIGN PATENT DOCUMENTS

| | | | |
|---|---|---|---|
| WO | 2007/081720 A | 7/2007 | |
| WO | WO 2007/081720 A2 | 7/2007 | |
| WO | 2008/104984 A | 9/2008 | |
| WO | WO 2008/104985 A2 | 9/2008 | |
| WO | 2008/117278 A | 10/2008 | |
| WO | 2009/057113 A | 5/2009 | |
| WO | 2009/153775 A2 | 12/2009 | |
| WO | WO 2009/153775 A2 | 12/2009 | |
| WO | WO2010/069129 A1 | 6/2010 | |
| WO | WO2010073248 | * 7/2010 | ............... C12Q 1/68 |

OTHER PUBLICATIONS

Cobb et al (Crit Care Med 2002 vol. 30 p. 2711).*
Cheung et al (Cold Spring Harbory Symposia on Quant Biol, 2003, vol. LXVIII, pp. 403-407).*
Hoshikawa et al (Physiol. Genomics, 2003, 12: 209-219).*
Enard et al. (Science 2002 vol. 296 p. 340).*
Extended European Search Report from corresponding patent application No. EP 12764700.6, dated Mar. 12, 2015, 18 pages.
Meiri, E., et al., "MicroRNAs as powerful diagnostic tools for the differential diagnosis of lung tumors". Internet article, Jun. 6, 2008, URL: http://www.mindcull.com/search.php?q=rosenwald&conferenceYear=ASCO+2008+-+American+Society+of+Clinical+Oncology&society=none> [retrieved on Oct. 1, 2009] the whole document.
Rosenfeld, N., et al., "MicroRNAs accurately identify cancer tissue origin," Nature Biotechnology, Nature Publishing Group, New York, NY, US, vol. 26, No. 4, Apr. 1, 2008, pp. 462-469, ISSN: 1087-0156, Abstract.
Yanaihara, et al., "Unique microRNA molecular profiles in lung cancer diagnosis and prognosis," Cancer Cell, Cell Press, US, vol. 9, No. 3, Mar. 1, 2006, pp. 189-198, XP002467444, ISSN: 1535-6108, p. 19, right-hand column.
Ladeiro, Y., et al., "23 MicroRNA profiling in hepatocellular tumors is associated to clinical features and oncogene/tumor supressor gene mutation", Journal of Hepatology, Munksgaard International Publishers, Copenhagen, DK, vol. 48, Jan. 1, 2008, p. S11, ISSN: 0168-8278 [retrieved on Jan. 1, 2008] abstract.
Anonymous, "NCI-H157" Internet Article, [Online], Sep. 18, 2006, retrieved from the Internet: URL:http://www.sanger.ac.uk/perl/genetics/CGP/core_line_viewer?action=sample&1d-911847> [retrieved on Oct. 2, 2009] the whole document.
International Search Report from published PCT Patent Application No. WO2009/0153775, dated Jan. 14, 2010, 7 pages.
Database Geneseq [Online] ebi; Nov. 2, 2000, Ulfendahl P, Wong K.; retrieved from http://srs.ebi,ac.uk, Database accession No. aac95969 abstract.
XP055153320, M Perelman et al.: "MicroRNA Biomarkers for Differential Diagnosis of Lung Tumars: Abstract 1630", Abstracts of the Annual Meeting of the United States and Canadian Academy of Pathology. Mar. 7-13, 2009. Boston, Massachusetts, USA Abstract 1630, Jan. 1, 2009.
S. Gilad, G. Lithwick-Yanai, et al., Classification of the four main types of lung cancer using a microRNA-based diagnostic assay, J Mol Diagn, vol. 14, No. 5, pp. 510-517 (2012).
C.F. Aliferis et al., Machine Learning Models for Lung Cancer Classification using Array Comparative Genomic Hybridization, AMIA, Annual Symposium Proceedings, pp. 7-11 (2002).

(Continued)

*Primary Examiner* — Sarae L Bausch
(74) *Attorney, Agent, or Firm* — Polsinelli, PC; Ron Galant

(57) ABSTRACT

The present invention provides specific nucleic acid sequences for use in the identification, classification and diagnosis of various sub-types of lung cancers. The present invention permits one to accurately classify lung cancers based on their miR expression profile without further manipulation. Using microRNA microarray data generated from over two hundred formalin-fixed paraffin-embedded (FFPE) resection samples, fine needle aspiration (FNA) samples and fine needle biopsy (FNB) samples of primary lung cancer, microRNA expression profiles were identified that differ significantly for various sub-types of lung cancer.

13 Claims, 12 Drawing Sheets

(56) References Cited

OTHER PUBLICATIONS

M. Burroni et al., Melanoma Computer-Aided Diagnosis: Reliability and Feasibility Study, Clinical Cancer Research, vol. 10, pp. 1881-1886 (2004).

* cited by examiner

METHODS FOR LUNG CANCER CLASSIFICATION

CROSS REFERENCE TO RELATED APPLICATIONS

The present application is a National Phase Application of PCT International Application PCT/IL2012/000131, filed Mar. 26, 2012, which claims priority, under 35 U.S.C. § 119(e), to and the benefit of U.S. Provisional Application No. 61/468,077 filed Mar. 28, 2011, all of which are herein incorporated by reference in their entirety.

FIELD OF THE INVENTION

The invention relates in general to microRNA molecules, as well as various nucleic acid molecules relating thereto or derived therefrom, associated with specific types of lung cancers.

BACKGROUND OF THE INVENTION

In recent years, microRNAs (miRs) have emerged as an important novel class of regulatory RNA, which have a profound impact on a wide array of biological processes.

These small (typically 18-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. There are currently about 1,220 known human miRs.

Classification of cancer has typically relied on the grouping of tumors based on histology, cytogenetics, immunohistochemistry, and known biological behavior. The pathologic diagnosis used to classify the tumor taken together with the stage of the cancer is then used to predict prognosis and direct therapy. However, current methods of cancer classification and staging are not completely reliable.

Lung cancer is one of the most common causes of cancer death worldwide, and non-small cell lung cancer (NSCLC) accounts for nearly 80% of those cases. Many genetic alterations associated with the development and progression of lung cancer have been reported, but the precise molecular mechanisms remain unclear.

The classification of lung tumors poses a diagnostic challenge and there is lack of standardized techniques for tumor subtyping which determines selection of treatment options. Moreover, in about 20% of cases a subclassification is not possible on preoperative specimens.

Making the correct diagnosis and specifically the distinction between primary lung cancers of squamous cell carcinoma, non-squamous NSCLC, carcinoid and small cell carcinoma has practical importance for choice of therapy. To-date there is no objective standardized test for accurate subclassification of lung cancers. Thus, there is an unmet need for a reliable method for distinguishing between specific lung cancers.

SUMMARY OF THE INVENTION

The present invention provides specific nucleic acid sequences for use in the identification, classification and diagnosis of various sub-types of lung cancers. The present invention permits one to accurately classify lung cancers based on their miR expression profile without further manipulation.

Using microRNA microarray data generated from over two hundred formalin-fixed, paraffin-embedded (FFPE) resection samples, fine needle aspiration (FNA) samples and fine needle biopsy (FNB) samples of primary lung cancer, microRNA expression profiles were identified that differ significantly for various sub-types of lung cancer. Based on these findings, a microRNA-based qRT-PCR assay was developed that differentiates primary lung cancers into four types: squamous cell carcinoma, non-squamous NSCLC carcinoid and small cell carcinoma. This assay can be used on resection specimens, small biopsies, FNA samples and cell blocks from cytology.

The invention further provides a method for distinguishing between specific subtypes of lung cancer, the method comprising: obtaining a biological sample from a subject; determining an expression profile of a nucleic acid sequence selected from the group consisting of SEQ ID NOS: 1-8, a fragment thereof and a sequence having at least about 80% identity thereto in said sample; and comparing said expression profile to a reference expression profile; wherein the comparison of said expression profile to said reference expression profile is indicative of said lung cancer.

According to some embodiments, said lung cancer is selected from the group consisting of squamous cell carcinoma, non-squamous NSCLC, carcinoid lung cancer and small cell lung carcinoma.

According to one embodiment, said nucleic acid sequence is selected from the group consisting of SEQ ID NOS: 3, 7, 8, a fragment thereof and a sequence having at least about 80% identity thereto, wherein relatively high expression levels of said nucleic acid sequence, as compared to said reference expression profile, is indicative of carcinoid lung cancer.

According to another embodiment, said nucleic acid sequence is selected from the group consisting of SEQ ID NOS: 1, a fragment thereof and a sequence having at least about 80% identity thereto, wherein relatively high expression levels of said nucleic acid sequence, as compared to said reference expression profile, is indicative of small cell lung cancer (SCLC).

According to one embodiment, said nucleic acid sequence is selected from the group consisting of SEQ ID NOS: 2, 5, 6, a fragment thereof and a sequence having at least about 80% identity thereto, wherein relatively high expression levels of said nucleic acid sequence, as compared to said reference expression profile, is indicative of non-squamous non-small cell lung cancer (NSCLC).

According to another embodiment, said nucleic acid sequence is selected from the group consisting of SEQ ID NOS: 4, a fragment thereof and a sequence having at least about 80% identity thereto, wherein relatively high expression levels of said nucleic acid sequence, as compared to said reference expression profile, is indicative of squamous cell carcinoma.

In certain embodiments, the subject is a human.

In certain embodiments, the method is used to determine a course of treatment of the subject.

According to some embodiments, the classification method of the present invention further comprises a classifier algorithm, said classifier algorithm is selected from the group consisting of K nearest neighbors classifier (KNN), logistic regression classifier, linear regression classifier, nearest neighbor classifier, neural network classifier, Gaussian mixture model (GMM) classifier and Support Vector Machine (SVM) classifier. The classifier may use a decision tree structure (including binary tree) or a voting (including weighted voting) scheme to compare one or more models which compare one or more classes to other classes.

According to some embodiments, said biological sample is selected from the group consisting of bodily fluid, a cell line and a tissue sample. According to some embodiments, said tissue is a fresh, frozen, fixed, wax-embedded or formalin fixed paraffin-embedded (FFPE) tissue. According to one embodiment, the tissue sample is a lung sample.

According to some embodiments, the method comprises determining the expression levels of at least two nucleic acid sequences. According to some embodiments the method further comprises combining one or more expression ratios. According to some embodiments, the expression levels are determined by a method selected from the group consisting of nucleic acid hybridization, nucleic acid amplification, and a combination thereof. According to some embodiments, the nucleic acid hybridization is performed using a solid-phase nucleic acid biochip array. According to certain embodiments, the nucleic acid hybridization is performed using in situ hybridization.

According to other embodiments, the nucleic acid amplification method is real-time PCR (RT-PCR). According to one embodiment, said real-time PCR is quantitative real-time PCR (qRT-PCR).

According to some embodiments, the RT-PCR method comprises forward and reverse primers. According to other embodiments, the forward primer comprises a sequence selected from the group consisting of any one of SEQ ID NOS: 9-16 and sequences at least about 80% identical thereto. According to some embodiments, the real-time PCR method further comprises hybridization with a probe. According to some embodiments, the probe comprising a nucleic acid sequence that is complementary to a sequence selected from selected from the group consisting of SEQ ID NOS: 1-8.

According to other embodiments, the probe comprises a sequence selected from the group consisting of SEQ ID NOS: 17-24, a fragment thereof and sequences at least about 80% identical thereto.

The invention further provides a kit for lung cancer classification, said kit comprises a probe comprising a nucleic acid sequence that is complementary to a sequence selected from the group consisting of SEQ ID NOS: 1-8, a fragment thereof and sequences having at least about 80% identity thereto. According to other embodiments the probe comprises a nucleic acid sequence selected from the group consisting of SEQ ID NOS: 17-24, and sequences having at least about 80% identity thereto.

According to other embodiments, the kit further comprises a forward primer comprising a sequence selected from the group consisting of SEQ ID NOS: 9-16 and sequences having at least about 80% identity thereto.

These and other embodiments of the present invention will become apparent in conjunction with the figures, description and claims that follow.

BRIEF DESCRIPTION OF THE DRAWINGS

FIGS. 11A-B are boxplot presentations comparing distributions of the expression of hsa-miR-29b (A, SEQ ID NO: 6), and a sequence similar to hsa-miR-29b: (B, SEQ ID NO: 48), in FFPE tumor samples obtained from patients: I-carcinoid lung cancer, II-small cell lung carcinoma, III-non-squamous NSCLC, IV-squamous cell carcinoma. The results are based on Real time PCR, and a higher normalized signal indicates higher expression of the miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.

DETAILED DESCRIPTION OF THE INVENTION

Figure 1A:
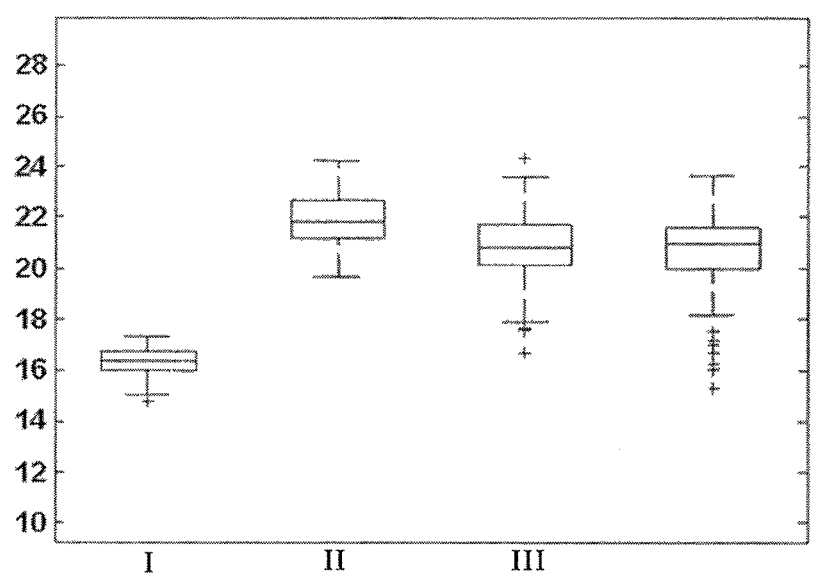
FIGS. 1A-B are boxplot presentations comparing distributions of the expression of hsa-miR-106a (SEQ ID NO: 1) in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.

The invention is based in part on the discovery that specific nucleic acid sequences (SEQ ID NOS: 1-8) and nucleic acid molecules relating thereto can be used for the identification, classification and diagnosis of specific lung cancers.

The present invention provides a sensitive, specific and accurate method which may be used to distinguish between various sub-types of lung cancers.

The methods of the present invention have high sensitivity and specificity. The possibility to distinguish between specific lung cancers facilitates providing the patient with the best and most suitable treatment.

The present invention provides diagnostic assays and methods, both quantitative and qualitative for detecting, diagnosing, monitoring, staging and prognosticating cancers by comparing levels of the specific microRNA molecules of the invention. Such levels are preferably measured in at least one of biopsies, tumor samples, cells, tissues and/or bodily fluids, including determination of normal and abnormal levels. The present invention provides methods for diagnosing the presence of a specific cancer by analyzing changes in levels of said microRNA molecules in biopsies, tumor samples, cells, tissues or bodily fluids.

In the present invention, determining the presence of said microRNA levels in biopsies, tumor samples, cells, tissues or bodily fluid, is particularly useful for discriminating between different types of lung cancers.

All the methods of the present invention may optionally include measuring levels of other cancer markers. Other cancer markers, in addition to said microRNA molecules, useful in the present invention will depend on the cancer being tested and are known to those of skill in the art.

Assay techniques that can be used to determine levels of gene expression, such as the nucleic acid sequence of the present invention, in a sample derived from a patient are well known to those of skill in the art. Such assay methods include, without limitation, radio immunoassays, reverse transcriptase PCR (RT-PCR) assays, immunohistochemistry assays, in situ hybridization assays, competitive-binding assays, Northern Blot analyses, ELISA assays and biochip analysis.

In some embodiments of the invention, correlations and/or hierarchical clustering can be used to assess the similarity of the expression level of the nucleic acid sequences of the invention between a specific sample and different exemplars of cancer samples, by setting an arbitrary threshold for assigning a sample or cancer sample to one of two groups. Alternatively, the threshold for assignment is treated as a parameter, which can be used to quantify the confidence with which samples are assigned to each class. The threshold for assignment can be scaled to favor sensitivity or specificity, depending on the clinical scenario. The correlation value to the reference data generates a continuous score that can be scaled.

Definitions

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

About

As used herein, the term "about" refers to +/−10%.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Attached

"Attached" or "immobilized" as used herein refer to a probe and a solid support and may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe, or both. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, neuroendocrine lung cancer (e.g., small cell lung cancer (SCLC), a large cell neuroendocrine carcinoma (LCNEC), a typical carcinoid (TC) neuroendocrine tumor, and an atypical carcinoid (AC) neuroendocrine tumor), non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Classification

"Classification" as used herein refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. According to one embodiment, classification means determination of the type of lung cancer.

Complement

"Complement" or "complementary" as used herein means Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Ct

Ct signals represent the first cycle of PCR where amplification crosses a threshold (cycle threshold) of fluorescence. Accordingly, low values of Ct represent high abundance or expression levels of the microRNA.

In some embodiments the PCR Ct signal is normalized such that the normalized Ct remains inversed from the expression level. In other embodiments the PCR Ct signal may be normalized and then inverted such that low normalized-inverted Ct represents low abundance or expression levels of the microRNA.

Detection

"Detection" means detecting the presence of a component in a sample. Detection also means detecting the absence of a component. Detection also means measuring the level of a component, either quantitatively or qualitatively.

Differential Expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, in situ hybridization and RNase protection.

Expression Profile

The term "expression profile" is used broadly to include a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 2, 5, 10, 20, 25, 50, 100 or more of, including all of the listed nucleic acid sequences. According to some embodiments, the term "expression profile" means measuring the abundance or the expression of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid or polypeptide. Thus, a fragment is itself also a nucleic acid or polypeptide, respectively.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Host Cell

"Host cell" as used herein may be a naturally occurring cell or a transformed cell that may contain a vector and may support replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO and HeLa.

Identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

K-Nearest Neighbor

The phrase "K-nearest neighbor" refers to a classification method that classifies a point by calculating the distances between it and points in the training data set. It then assigns the point to the class that is most common among its K-nearest neighbors (where K is an integer).

Label

"Label" as used herein means a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression allows one to predict a discrete outcome, such as group membership, from a set of variables that may be continuous, discrete, dichotomous, or a mix of any of these. The dependent or response variable is dichotomous, for example, one of two possible types of cancer. Logistic regression models the natural log of the odds ratio, i.e. the ratio of the probability of belonging to the first group (P) over the probability of belonging to the second group (1−P), as a linear combination of the different expression levels (in log-space) and of other explaining variables. The logistic regression output can be used as a classifier by prescribing that a case or sample will be classified into the first type if P is greater than 0.5 or 50%. Alternatively, the calculated probability P can be used as a variable in other contexts such as a 1D or 2D threshold classifier.

1D/2D Threshold Classifier

"1D/2D threshold classifier" used herein may mean an algorithm for classifying a case or sample such as a cancer sample into one of two possible types such as two types of cancer or two types of prognosis (e.g. good and bad). For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A score may be calculated as a function (usually a continuous function) of the two variables; the decision is then reached by comparing the score to the predetermined threshold, similar to the 1D threshold classifier.

Nucleic Acid

"Nucleic acid" or "oligonucleotide" or "polynucleotide" as used herein mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methyl-phosphoroamidite linkages and peptide nucleic acid backbones and linkages. Other analog nucleic acids include those with positive backbones; non-ionic backbones, and non-ribose backbones, including those described in U.S. Pat.

Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005) and Soutschek et al., Nature 432:173-178 (2004), which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Promoter

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

Reference Expression Profile

As used herein the term "reference expression profile" means a value that statistically correlates to a particular outcome when compared to an assay result. In preferred embodiments the reference value is determined from statistical analysis of studies that compare microRNA expression with known clinical outcomes. The reference value may be a threshold score value or a cutoff score value. Typically a reference value will be a threshold above which one outcome is more probable and below which an alternative threshold is more probable.

Selectable Marker

"Selectable marker" as used herein means any gene which confers a phenotype on a host cell in which it is expressed to facilitate the identification and/or selection of cells which are transfected or transformed with a genetic construct. Representative examples of selectable markers include the ampicillin-resistance gene ($Ame^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptll), hygromycin-resistance gene, beta-glucuronidase (GUS) gene, chloramphenicol acetyltransferase (CAT) gene, green fluorescent protein (GFP)-encoding gene and luciferase gene.

Sensitivity

"sensitivity" used herein may mean a statistical measure of how well a binary classification test correctly identifies a condition, for example how frequently it correctly classifies a cancer into the correct type out of two possible types. The sensitivity for class A is the proportion of cases that are determined to belong to class "A" by the test out of the cases that are in class "A", as determined by some absolute or gold standard.

Specificity

"Specificity" used herein may mean a statistical measure of how well a binary classification test correctly identifies a condition, for example how frequently it correctly classifies a cancer into the correct type out of two possible types. The specificity for class A is the proportion of cases that are determined to belong to class "not A" by the test out of the cases that are in class "not A", as determined by some absolute or gold standard.

Stringent Hybridization Conditions "Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium).

Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15,16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. No. 11/384,049, 11/418,870 or 11/429,720, the contents of which are incorporated herein.

Threshold Expression Level

As used herein, the phrase "threshold expression level" refers to a criterion expression value to which measured values are compared in order to determine the specific type of lung cancer. The reference expression profile may be based on the expression level of the nucleic acids, or may be based on a combined metric score thereof.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Vector

"Vector" as used herein means a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Wild Type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

The present invention employs miRNA for the identification, classification and diagnosis of specific lung cancers.

MicroRNA Processing

A gene coding for a microRNA (miRNA) may be transcribed leading to production of an miRNA precursor known as the pri-miRNA. The pri-miRNA may be part of a polycistronic RNA comprising multiple pri-miRNAs. The pri-miRNA may form a hairpin structure with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nucleotide precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of the stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repression or activation), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA: miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have studied the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85).

Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and the binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acids

Nucleic acids are provided herein. The nucleic acids comprise the sequence of SEQ ID NOS: 1-61 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000, 100-20,000, 1,000-1, 500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-8, 26-37, 38-49; or variants thereof.

The pri-miRNA may form a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole, as calculated by the Vienna algorithm, with default parameters as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-8, 26-37, 38-49; or variants thereof.

miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-8, 38-42, 48; or variants thereof.

Anti-miRNA

The nucleic acid may also comprise a sequence of an anti-miRNA capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-8, 38-42, 48; or variants thereof.

Binding Site of Target

The nucleic acid may also comprise a sequence of a target microRNA binding site or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the sequence of SEQ ID NOS: 1-8, 38-42, 48.

Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), P3×63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

Probes

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

Test Probe

The probe may be a test probe. The test probe may comprise a nucleic acid sequence that is complementary to a miRNA, a miRNA*, a pre-miRNA, or a pri-miRNA. The sequence of the test probe may be selected from SEQ ID NOS: 17-24 and 56-61.

Linker Sequences

The probe may further comprise a linker. The linker may be 10-60 nucleotides in length.

The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

Reverse Transcription

Target sequences of a cDNA may be generated by reverse transcription of the target RNA. Methods for generating cDNA may be reverse transcribing polyadenylated RNA or alternatively, RNA with a ligated adaptor sequence.

Reverse Transcription using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Reverse Transcription using Polyadenylated Sequence Ligated to RNA

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines. The reverse transcription primer may comprise SEQ ID NO: 25.

RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

Forward Primer

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides. The forward primer may comprise SEQ ID NOS: 9-16, 50-55.

Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise 12-24 nucleotides.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined locations on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrate materials include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The substrate of the biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker.

The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostics

A method of diagnosis is also provided. The method comprises detecting a differential expression level of lung specific cancer-associated nucleic acids in a biological sample. The sample may be derived from a patient. Diagnosis of a cancer state, and its histological type, in a patient may allow for prognosis and selection of therapeutic strategy. Further, the developmental stage of cells may be classified by determining temporarily expressed cancer-associated nucleic acids.

In situ hybridization of labeled probes to tissue sections or smears may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be used for the amplification, detection, identification or quantification of a target nucleic acid sequence. The kit may comprise a poly(T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus, may include, for example, a solid support.

The following examples are presented in order to more fully illustrate some embodiments of the invention. They should, in no way be construed, however, as limiting the broad scope of the invention.

EXAMPLES

Example 1

Experimental Procedures

1. Tumor Samples 229 formalin-fixed paraffin embedded (FFPE) resections, FNA and FNB from different histological subtypes of lung cancer samples (Table 1) were obtained from the following sources: Sheba Medical Center, Tel Hashomer, Israel; Rabin Medical Center, Petah Tikva, Israel; and ABS Inc., Wilmington, Del. Institutional review approvals were obtained for all samples in accordance with each institute's institutional review board or IRB-equivalent guidelines.

TABLE 1

| Tumor samples | | | | |
|---|---|---|---|---|
| | Resection | FNB | FNA | Total |
| Small | 16 | 6 | 23 | 45 |
| Carcinoid | 27 | 0 | 0 | 27 |
| NonSquamous | 42 | 4 | 33 | 79 |
| Squamous | 36 | 12 | 30 | 78 |
| Total | 121 | 22 | 86 | 229 |

2. miR Array Platform

MicroRNA profiling was performed on a set of 50 resection samples (11 small, 15 carcinoid, 15 non-squamous NSCLC, 9 squamous) that overlap with the resection samples listed in Table 1. Profiling was performed using both in-house custom microRNA microarrays and Agilent custom microRNA microarrays. In the in-house microarrays, 747 DNA oligonucleotide probes representing nearly 700 microRNAs listed in the Sanger database as well as additional microRNAs predicted and validated by Rosetta Genomics and controls, were spotted in triplicate using the BioRobotics MicroGrid II microarrater (Genomic Solutions, Ann Arbor, Mich.) according to the manufacturer's directions on slide E coated microarray slides (Schott Nexterion, Mainz, Germany). For the Agilent custom microRNA microarrays, around 900 microRNAs were printed.

Negative control probes were designed using the sense sequences of a set of microRNAs. Two groups of positive control probes were included on the slide: (i) probes designed to detect synthetic small RNAs that were spiked into each sample before labeling and thus verify labeling efficiency and (ii) probes designed to detect abundant small RNAs that indicate RNA quality. 3.5 μg of total RNA was labeled by ligation to an RNA-linker, p-rCrU-Cy/dye (Dharmacon, Lafayette, Colo.), which had Cy3 or Cy5 at its 3'-end. Each RNA sample was hybridized independently to a slide by incubation for 12-16 hours at 42° C. and then the slides washed twice. Arrays were scanned using Agilent DNA Microarray Scanner Bundle (Agilent Technologies, Santa Clara, Calif.) at a resolution of 10 μm at 100% power. Array images were analyzed and raw data extracted using SpotReader software (Niles Scientific, Portola Valley, Calif.).

3. RNA Extraction

RNA was extracted from formalin fixed paraffin-embedded (FFPE) tissues according to the following protocol:

1 ml Xylene (Biolab) was added to 1-2 mg tissue, incubated at 57° C. for 5 min and centrifuged for 2 min at 10,000 g. The supernatant was removed and 1 ml Ethanol (100%) (Biolab) was added. Following centrifugation for 10 min at 10,000 g, the supernatant was discarded and the washing procedure was repeated. Following air drying for 10-15 min, 500 μl Buffer B (NaCl 10 mM, Tris pH 7.6, 500 mM, EDTA 20 mM, SDS 1%) and 5 μl proteinase K (50 mg/ml) (Sigma) were added. Following incubation at 45° C. for 16 h, inactivation of the proteinase K at 100° C. for 7 min was preformed. Following extraction with acid phenol chloroform (1:1) (Sigma) and centrifugation for 10 min at maximum speed at 4° C., the upper phase was transferred to a new tube with the addition of 3 volumes of 100% Ethanol, 0.1 volume of NaOAc (BioLab) and 8 μl glycogen (Ambion) and left over night at −20° C.

Following centrifugation at maximum speed for 40 min at 4° C., washing with 1 ml Ethanol (85%), and drying, the RNA was re-suspended in 45 μl DDW.

The RNA concentration was tested and DNase Turbo (Ambion) was added accordingly (1 μl DNase/10 μg RNA). Following Incubation for 30 min at room temperature and extraction with acid phenol chloroform, the RNA was re-suspended in 45 μl DDW. The RNA concentration was tested again and DNase Turbo (Ambion) was added accordingly (1 μl DNase/10 μg RNA). Following incubation for 30 min at room temperature and extraction with acid phenol chloroform, the RNA was re-suspended in 20 μl DDW.

4. RNA Polyadenylation and Annealing of Poly(T) Adapter

A mixture was prepared according to the following:

| Component | Vol/sample |
|---|---|
| PNK buffer (NEB) | 1 μl |
| 25 mM MnCl$_2$ (Sigma) | 1 μl |

-continued

| Component | Vol/sample |
|---|---|
| 10 mM ATP (Promega) | 2 µl |
| Poly A polymerase (Takara) | 1 µl |
| Total Vol | 5 µl |

5 µl of the mixture were added to 5 µl of appropriate RNA sample (1 µg) (or to the ultra pure water of the No RNA control). The reaction was incubated for 1 hour at 37° C. Poly(T) adapter mixture was prepared according to the following:

| Component | Vol/sample |
|---|---|
| 0.5 µg/µl Poly(T) adapter (IDT) | 1 µl |
| Ultra pure water | 2 µl |
| Total Vol | 3 µl |

3 µl from the Poly(T) adapter mixture and 5 µl from the poly-adenylated RNA or negative control were transferred to PCR tubes. Annealing process was performed by the following annealing program:
STEP 1: 85° C. for 2 min
STEP 2: 70° C. to 25° C.-decrease of 1° C. in each cycle for 20 sec.

5. Reverse Transcription
Reverse Transcription mixture was prepared according to the following:

| Component | Vol/sample |
|---|---|
| 5 × RT buffer (Invitrogen) | 4 µl |
| Trehalose D 1.7 M (Calbiochem, Sigma) | 3 µl |
| 10 mM dNTPs mix (Promega) | 1 µl |
| DTT (0.1 M) (Invitrogen) | 2 µl |
| Total Vol | 10 µl |

1.5 µl Recombinant Rnasin (Promega) and 1 µl superscript II RT (Invitrogen) were added to the above mixture. 12.5 µl of the mix were added to each PCR tube containing the annealed PolyA RNA and to the No RNA control.

The tubes were inserted into a PCR instrument (MJ Research Inc.) and the following program was performed:
STEP 1: 37° C. for 5 min
STEP 2: 45° C. for 5 min
STEP 3: Repeat steps 1-2, 5 times
STEP 4: End the program at 4° C.

The cDNA microtubes were stored at −20° C.

6. Real Time PCR Using MGB Probe
Each cDNA sample was evaluated in triplicate for the following:
A primer-probe mix was prepared. In each tube 10 µM Fwd primer with the same volume of 5 µM of the corresponding MGB probe (ABI) specific for the same RNA were mixed. The sequences of the Fwd primers and MGB probes are indicated in Table 2.

TABLE 2

Sequences of the nucleic acid sequences of the present invention

| miR name | miR SEQ ID NO: | hairpin SEQ ID NO: | Forward primer | FWD SEQ ID NO: | MGB probes | Probe SEQ ID NO: |
|---|---|---|---|---|---|---|
| hsa-miR-106a | 1 | 26 | CAGTCATTTGGAAAAGTGCTTACAGTGCA | 9 | CCGTTTTTTTTTTTCTACCTGC | 17 |
| hsa-miR-125a-5p | 2 | 27 | GCTCCCTGAGACCCTTTAACCTGT | 10 | AAAACCGATAGTGAGTCG | 18 |
| hsa-miR-129-3p | 3 | 28, 29 | GCAAGCCCTTACCCCAAAAAGCAT | 11 | AAAACCGATAGTGAGTCG | 19 |
| hsa-miR-205 | 4 | 30 | CAGTCATTTGGCTCCTTCATTCCACCGGA | 12 | CGTTTTTTTTTTTCAGACTCC | 20 |
| hsa-miR-21 | 5 | 31 | CAGTCATTTGGCTAGCTTATCAGACTGA | 13 | CCGTTTTTTTTTTTCAACATCA | 21 |
| hsa-miR-29b | 6 | 32, 33 | CATTTGGTAGCACCATTTGAAATCAGTGTT | 14 | AAAACCGATAGTGAGTCG | 22 |
| hsa-miR-375 | 7 | 34 | CAGTCATTTGGGTTTGTTCGTTCGGCTC | 15 | CCGTTTTTTTTTTTCACGCGAG | 23 |
| hsa-miR-7 | 8 | 35, 36, 37 | CAGTCATTTGGCTGGAAGACTAGTGATT | 16 | CCGTTTTTTTTTTTACAACAAA | 24 |
| hsa-miR-17 | 38 | 43 | CAGTCATTTGGCCAAAGTGCTTACAGTG | 50 | CCGTTTTTTTTTTTCTACCTGC | 56 |
| hsa-miR-20a | 39 | 44 | CAGTCATTTGGTAAAGTGCTTATAGTGCA | 51 | CCGTTTTTTTTTTTCTACCTGC | 57 |
| hsa-miR-93 | 40 | 45 | CAGTCATTTGGCCAAAGTGCTGTTCGTG | 52 | CCGTTTTTTTTTTTCTACCTGC | 58 |
| hsa-miR-18a | 41 | 46 | CAGTCATTTGGCTAAGGTGCATCTAGTG | 53 | CCGTTTTTTTTTTTCTATCTGC | 59 |
| hsa-miR-18b | 42 | 47 | CAGTCATTTGGCTAAGGTGCATCTAGTG | 54 | CCGTTTTTTTTTTTCTAACTGC | 60 |
| hsa-miR-29c | 48 | 49 | CAGTCATTTGGCTAGCACCATTTGAAAT | 55 | CCGTTTTTTTTTTTAACCGATT | 61 |
| Reverse Primer | 25 | | | | | |

The cDNA was diluted to a final concentration of 0.5 ng/µl. PCR mixture was prepared according to the following:

| Component | Vol per well |
|---|---|
| 2 × TaqMan Universal PCR (ABI) | 10 µl |
| RT-rev-primer-Race 10 µM (IDT) | 1 µl |
| Ultra pure water | 6 µl |
| Total Vol | 17 µl |

68 µl (for No RNA control and for No cDNA control) or 170 µl of the PCR mix were dispensed into the appropriately labeled microtubes. 10 µl cDNA (0.5 ng/µl) were added into the appropriately labeled microtubes containing the mix. The PCR plates were prepared by dispensing 18 µl from the mix into each well. 2 µl of primer probe mixture were added into each well using a PCR-multi-channel. The plates were loaded in a Real Time-PCR instrument (Applied Biosystems) and the following program was performed:
Stage 1, Reps=1
STEP 1: Hold @ 95.0 for 10 min (MM:SS), Ramp Rate=100
Stage 2, Reps=40
STEP 1: Hold @ 95.0 for 0:15 (MM:SS), Ramp Rate=100
STEP 2: Hold @ 60.0 for 1:00 (MM:SS), Ramp Rate=100
Standard 7500 Mode
Sample Volume (µL): 20.0
Data Collection: Stage 2, Step 2

7. miR Array Data Normalization

The initial data set consisted of signals measured for multiple probes for every sample. For the analysis, signals were used only for probes that were designed to measure the expression levels of known or validated human microRNAs.

Triplicate spots were combined into one signal by taking the logarithmic mean of the reliable spots. All data was log-transformed and the analysis was performed in log-space. A reference data vector for normalization, R, was calculated by taking the mean expression level for each probe in two representative samples, one from each tumor type, for example: Neuroendocrine lung tumors and NSCLC.

For each sample k with data vector $S^k$, a 2nd degree polynomial $F^k$ was found so as to provide the best fit between the sample data and the reference data, such that $R \approx F^k(S^k)$. Remote data points ("outliers") were not used for fitting the polynomials F. For each probe in the sample (element $S_i^k$ in the vector $S^k$), the normalized value (in log-space) $M_i^k$ is calculated from the initial value $S_i^k$ by transforming it with the polynomial function $F^k$, so that $M_i^k = F^k(S_i^k)$. Statistical analysis is performed in log-space. For presentation and calculation of fold-change, data is translated back to linear-space by taking the exponent.

In order to calculate the p-value and the median fold-change for each miR in qRT-PCR data, the miR expression was normalized within each sample. This was performed by calculating a scaling factor as the average miR Ct within a sample subtracted by the average miR Ct over all samples. This scaling factor was them subtracted from the Ct each miR within the sample. Since higher Ct values for a miR are associated with lower abundance, the normalized expression of a miR was computed by subtracting this result from 50, in order to associate higher expression values with higher abundance.

8. Statistical Analysis

The purpose of this statistical analysis was to find probes whose normalized signal levels differ significantly between the two compared sample sets. Probes that had normalized signal levels in the microarray data below 300 in the two sample sets were not analyzed. For each probe, two groups of normalized signals obtained for two sample sets were compared. The p-value was calculated for each probe, using the statistical un-paired two-sided t-test method. The p-value is the probability for obtaining, by chance, the measured signals or a more extreme difference between the groups, had the two groups of signals come from distributions with equal mean values. microRNAs whose probes had the lowest and most significant t-test p-values were selected. A p-value lower than the threshold of 0.05 means that the probability that the two groups come from distributions with the same mean is lower than 0.05 or 5%, under the assumption of normal (Gaussian) log signal distributions. The two groups of signals are likely to result from distributions with different means, and the relevant microRNA is likely to be differentially expressed between the two sets of samples.

In some cases a different threshold was used, based on a statistical correction for multiple hypotheses testing, using the False Discovery Rate (FDR) method. In this case the threshold for identifying miRs which are likely to be differentially expressed was selected based on the number of miRs tested and the distribution of their p-values. Accuracy of classification or identification of sample types was assessed using the Response Operator Curve (ROC) which plots the sensitivity against (1-specificity), and by calculating the Area Under the Curve (AUC) of the ROC. Optimal identification is reached when both specificity and sensitivity reach 100%, giving rise to AUC=1.

9. miR RT-PCR Data Normalization

The cycle threshold ($C_T$, the PCR cycle at which probe signal reaches the threshold) was determined for each microRNA. Each sample was normalized by subtracting from the $C_t$ of each microRNA the average $C_t$ of all microRNAs of the sample, and adding back a scaling constant (the average $C_t$ over the entire sample set). Each value received was subtracted from 50.

10. Description of Classification Algorithm (KNN)

Classification was performed using the k-nearest neighbour algorithm, using k=9. In short, given a sample to classify: the pearson correlation coefficient was calculated for the sample with all the other samples over the eight miRs, using the non-normalized Ct values. The nine samples with the best correlation were taken and the histological class with the highest representation within this group of nine "neighbours" was used to determine the histological class of the sample being classified.

Example 2

Figure 1B:
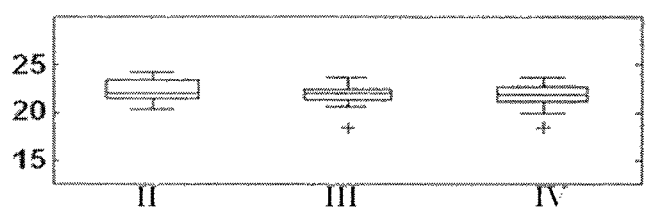
Figure 2A:
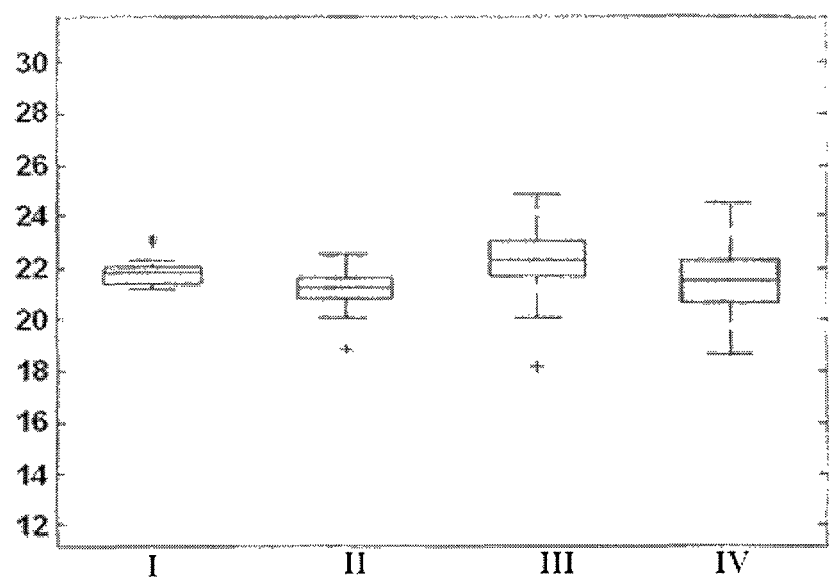
FIGS. 2A-B are boxplot presentations comparing distributions of the expression of hsa-miR-125a-5p (SEQ ID NO: 2), in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 2B:
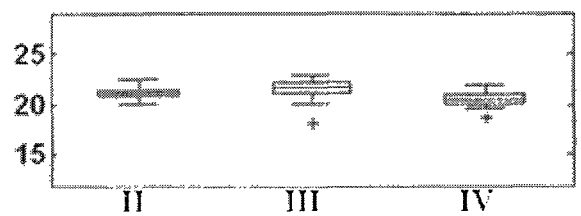
Figure 3A:
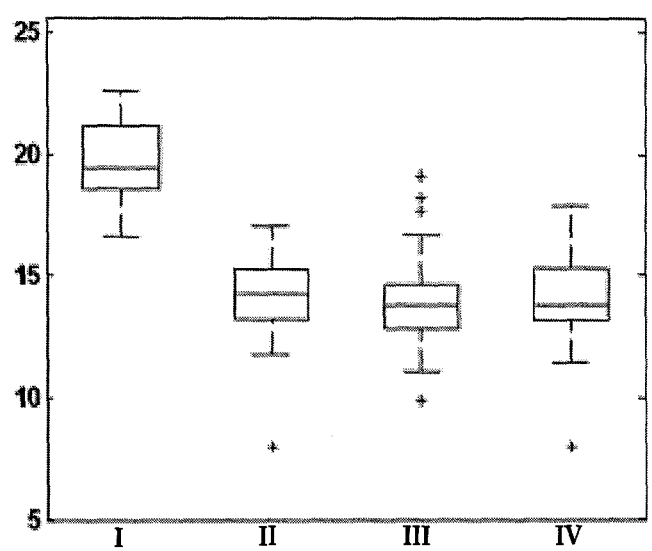
FIGS. 3A-B are boxplot presentations comparing distributions of the expression of hsa-miR-129-3p (SEQ ID NO: 3), in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 3B:
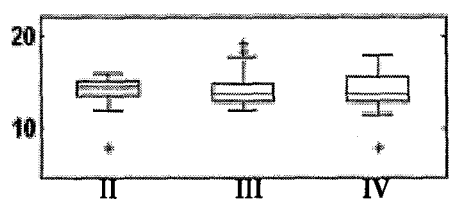
Figure 4A:
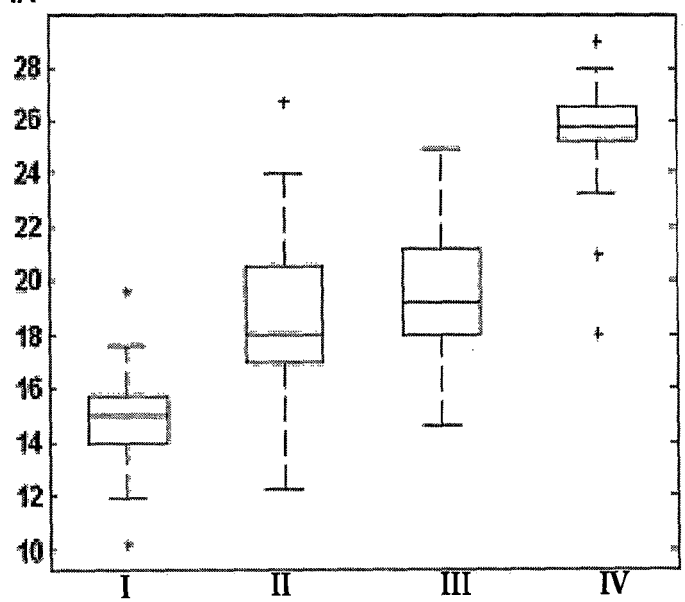
FIGS. 4A-B are boxplot presentations comparing distributions of the expression of hsa-miR-205 (SEQ ID NO: 4), in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 4B:
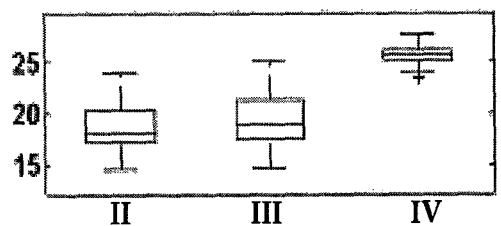
Figure 5A:
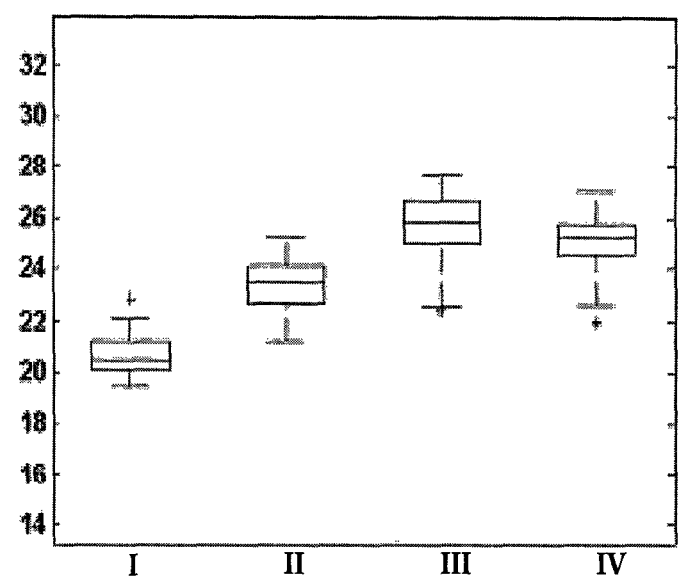
FIGS. 5A-B are boxplot presentations comparing distributions of the expression of hsa-miR-21 (SEQ ID NO: 5), in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 5B:
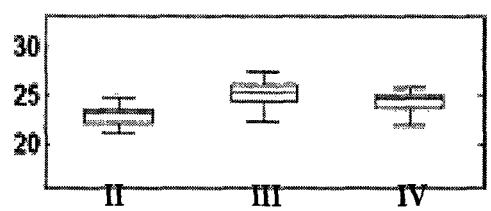
Figure 6A:
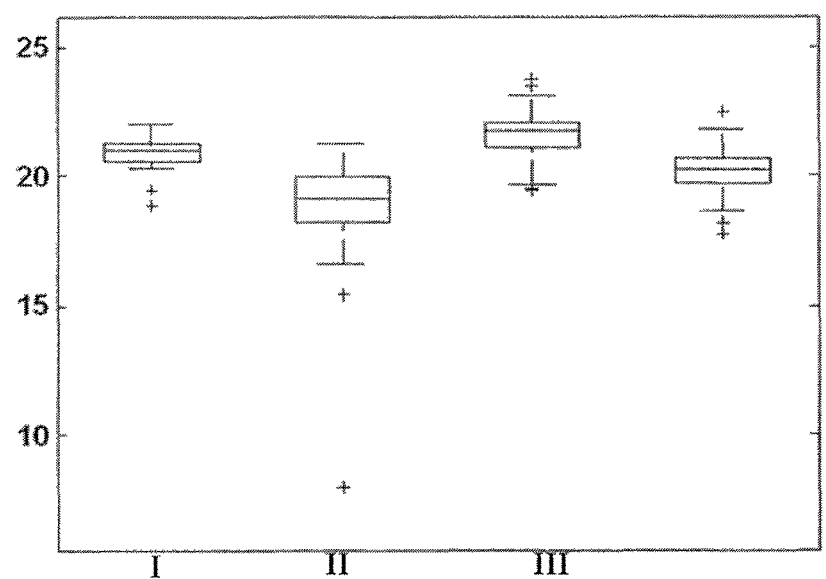
FIGS. 6A-B are boxplot presentations comparing distributions of the expression of hsa-miR-29b (SEQ ID NO: 6), in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 6B:
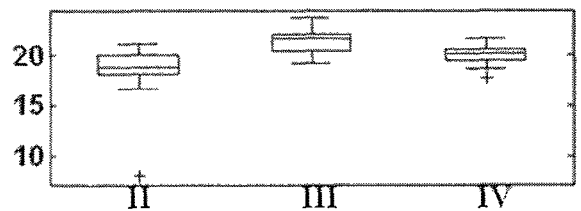
Figure 7A:
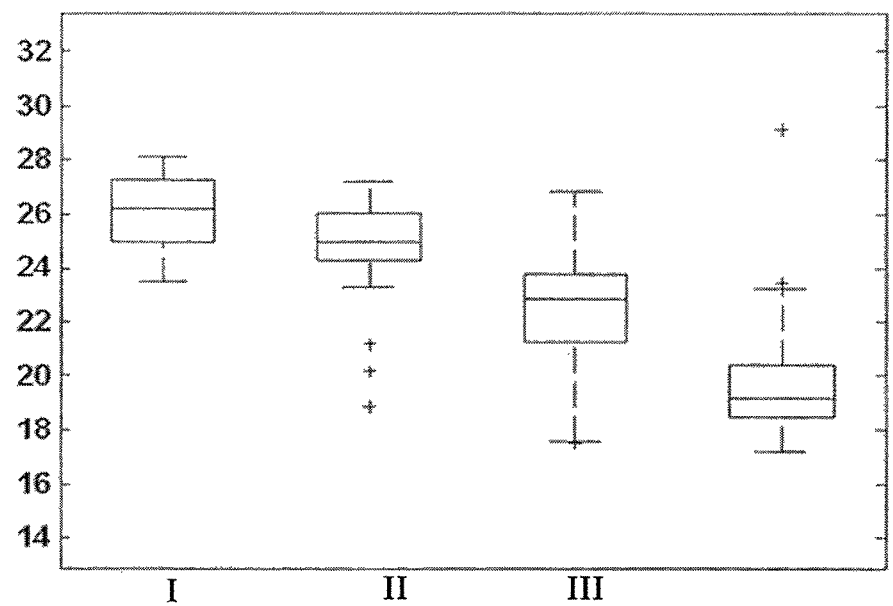
FIGS. 7A-B are boxplot presentations comparing distributions of the expression of hsa-miR-375 (SEQ ID NO: 7), in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 7B:
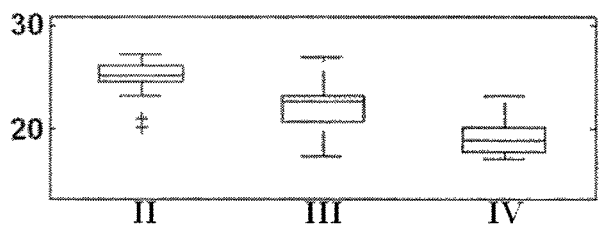
Figure 8A:
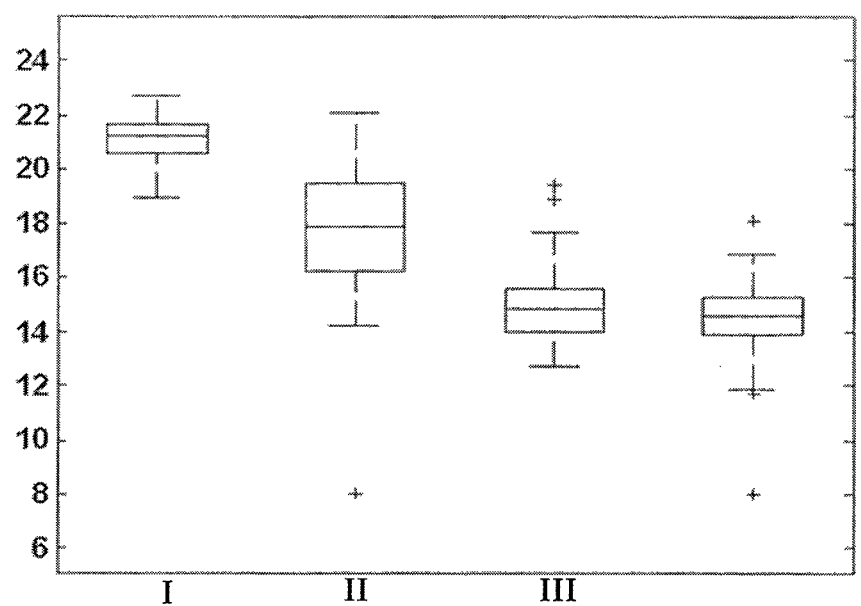
FIGS. 8A-B are boxplot presentations comparing distributions of the expression of hsa-miR-7 (SEQ ID NO: 8), in tumor samples (A-FFPE+FNA+FNB, B-FNA) obtained from patients: I-carcinoid lung cancer, II-small cell lung carcinoma, III-non-squamous non-small cell lung cancer (NSCLC), IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 8B:
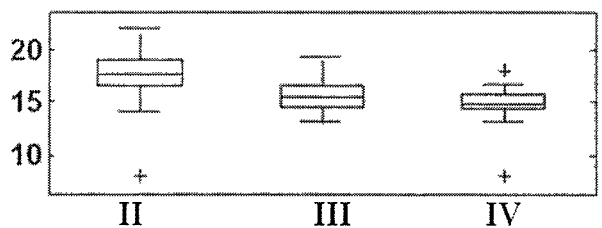
Figure 9:
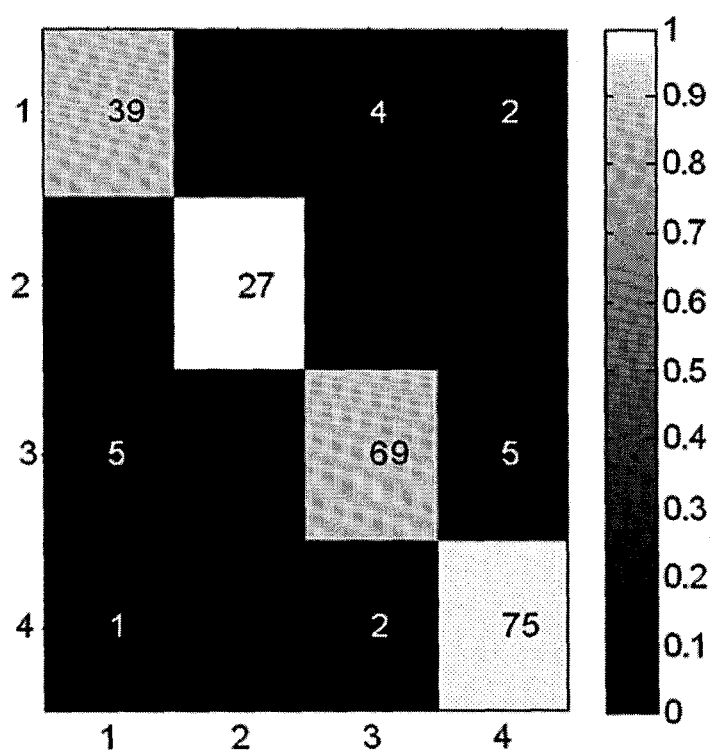
FIG. 9 is a confusion matrix showing the classification results. Each sample was classified using all the other samples. The y-axis shows the class of the samples as determined by pathological review ("Real class"): 1—small cell lung carcinoma, 2—carcinoid lung cancer, 3—non-squamous NSCLC 4—squamous cell carcinoma. The x-axis shows the resulting classification. The numbers of samples for each classification—"Real class" pair are shown. Entries in the matrix without a number indicate that no samples with the corresponding class received the corresponding classification. The overall accuracy was 91.7%. The sensitivities were 87% for small cell lung carcinoma, 100% for carcinoid lung cancer, 96% for squamous cell carcinoma and 87% for non-squamous NSCLC. The sensitivities for FNA samples were 87% for small cell lung carcinoma, 97% for squamous cell carcinoma and 76% for non-squamous NSCLC.

Specific MicroRNAs are Able to Distinguish Between Various Types of Lung Tumor Samples The real time PCR quantitation analysis of miRs differentially expressed between the various types of lung tumor samples are presented in Table 3. The results exhibited a significant difference in the expression pattern of the specific miRs as indicated in Table 3 and FIGS. 1-9.

TABLE 3

Normalized miR expression as measured by RT-PCR distinguishing between different subtypes of lung tumor samples

| miR name | Carcinoid vs Small | | Carcinoid vs NonSquamous | |
|---|---|---|---|---|
| | Fold-change | P-value | Fold-change | P-value |
| hsa-miR-106a | 48.5 | 5.46E−38 | 22.2 | 7.65E−28 |
| hsa-miR-125a-5p | 1.5 | 0.000447 | 1.45 | 0.0031 |
| hsa-miR-129-3p | 36.4 | 5.31E−22 | 53 | 2.90E−31 |
| hsa-miR-205 | 7.83 | 4.32E−08 | 17.4 | 1.22E−16 |
| hsa-miR-21 | 7.75 | 3.17E−18 | 45 | 2.40E−38 |
| hsa-miR-29b | 4.53 | 4.35E−07 | 1.7 | 1.33E−05 |
| hsa-miR-375 | 1.83 | 0.00634 | 10.3 | 2.34E−18 |
| hsa-miR-7 | 8.84 | 4.25E−08 | 89.3 | 2.32E−45 |

| miR name | Carcinoid vs Squamous | | Small vs NonSquamous | |
|---|---|---|---|---|
| | Fold-change | P-value | Fold-change | P-value |
| hsa-miR-106a | 25 | 2.25E−24 | 2.18 | 5.70E−06 |
| hsa-miR-125a-5p | 1.28 | 0.0878 | 2.18 | 1.48E−09 |
| hsa-miR-129-3p | 51.6 | 5.44E−28 | 1.46 | 0.437 |
| hsa-miR-205 | 1.73E+03 | 2.50E−55 | 2.22 | 0.00509 |
| hsa-miR-21 | 27.2 | 1.02E−36 | 5.81 | 1.32E−21 |
| hsa-miR-29b | 1.71 | 0.000686 | 7.67 | 2.11E−20 |
| hsa-miR-375 | 130 | 6.33E−41 | 5.64 | 9.20E−18 |
| hsa-miR-7 | 97.5 | 3.68E−38 | 10.1 | 9.68E−17 |

| miR name | Small vs Squamous | | NonSquamous vs Squamous | |
|---|---|---|---|---|
| | Fold-change | P-value | Fold-change | P-value |
| hsa-miR-106a | 1.94 | 2.03E−05 | 1.12 | 0.861 |
| hsa-miR-125a-5p | 1.17 | 0.324 | 1.85 | 4.70E−08 |
| hsa-miR-129-3p | 1.42 | 0.97 | 1.03 | 0.397 |
| hsa-miR-205 | 220 | 1.58E−42 | 99.2 | 1.35E−47 |
| hsa-miR-21 | 3.51 | 2.89E−15 | 1.66 | 5.57E−05 |
| hsa-miR-29b | 2.64 | 1.05E−08 | 2.91 | 1.21E−19 |
| hsa-miR-375 | 71.2 | 8.26E−47 | 12.6 | 1.84E−28 |
| hsa-miR-7 | 11 | 4.95E−17 | 1.09 | 0.0806 | miR name: is the miRBase registry name (release 15)
fold-change: is the fold change between the medians of the two groups
p-value: is the result of the un-paired two-sided t-test between samples Example 3 microRNA Similarity

Figure 10A:
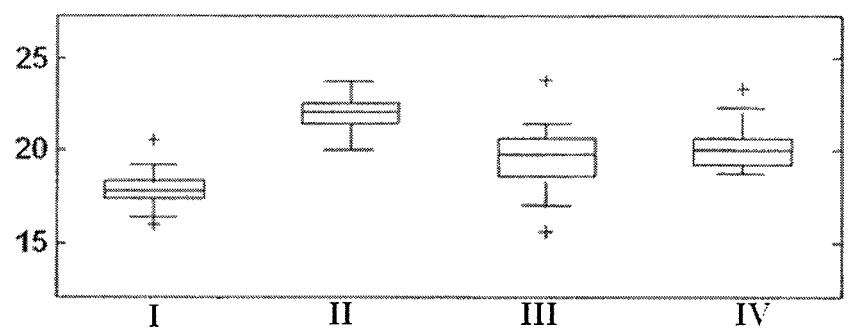
FIGS. 10A-F are boxplot presentations comparing distributions of the expression of hsa-miR-106a (A, SEQ ID NO: 1), and sequences similar to hsa-miR-106a: hsa-miR-17 (B, SEQ ID NO: 38), hsa-miR-20a (C, SEQ ID NO: 39), hsa-miR-93 (D, SEQ ID NO: 40), hsa-miR-18a (E, SEQ ID NO: 41), and hsa-miR-18b (F, SEQ ID NO: 42) in FFPE tumor samples obtained from patients: I-carcinoid lung cancer, II-small cell lung carcinoma, III-non-squamous NSCLC, IV-squamous cell carcinoma. The results are based on Real time PCR, and a higher normalized signal indicates higher expression of miR present in the samples. The line in the box indicates the median value. The box top and bottom boundaries indicate the $25^{th}$ and $75^{th}$ percentile. The horizontal lines and crosses (outliers whose distance from top or bottom box boundary is more than 1.5 times the height of the box) show the full range of signals in this group.
Figure 10B:
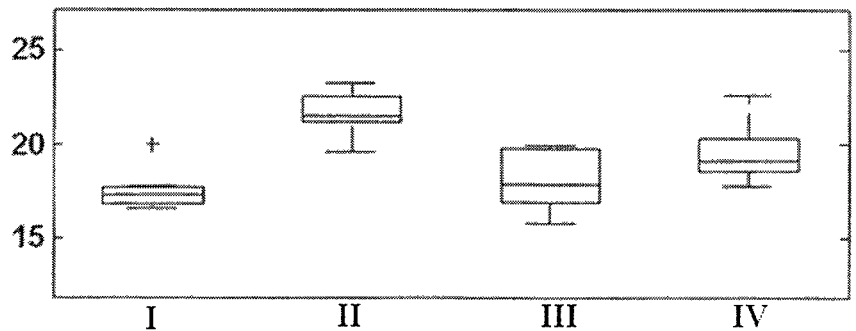
Figure 10C:
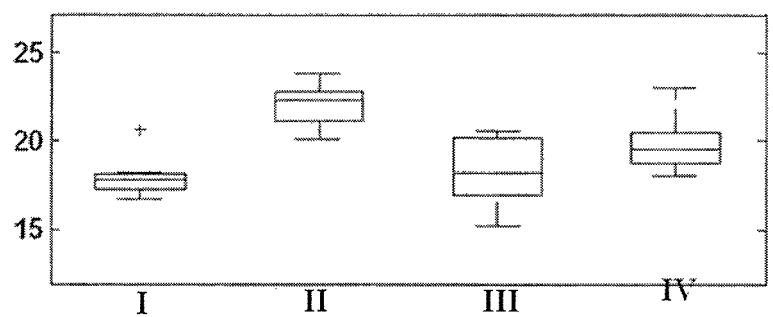
Figure 10D:
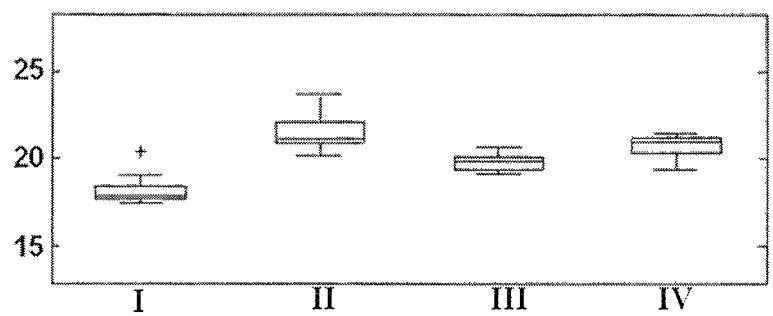
Figure 10E:
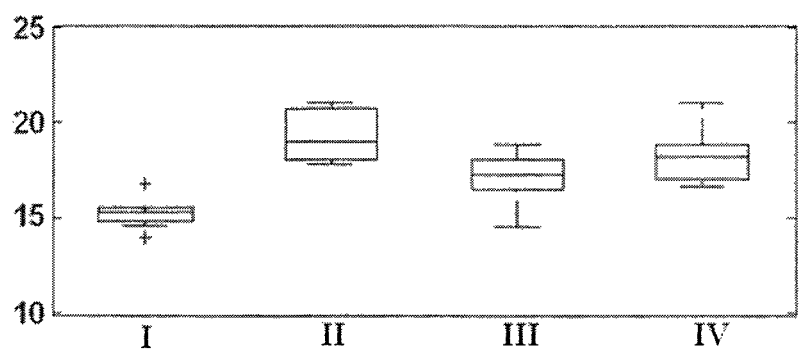
Figure 10F:
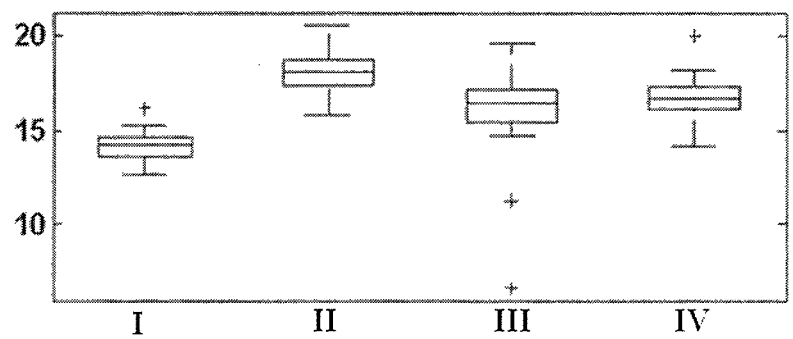

For a set of 38 resection samples (10 Carcinoid, 9 Small, 10 NonSquamous, 9 Squamous), RT-PCR was also performed for sequences similar to hsa-miR-106a and hsa-miR-29b. For hsa-miR-106a, 5 miRs with similarity ranging from 73.9% to 95.6% were examined. For hsa-miR-29b, one miR, with similarity 86.4%, was examined. As shown in Table 4 and FIGS. 10-11, for both miRs, the similar miRs have similar expression trends.

TABLE 4

Normalized miR expressionas measured by RT-PCR in similar sequences

| miR name | % similarity to hsa-miR-106a | Carcinoid vs Small | | Carcinoid vs NonSquamous | |
|---|---|---|---|---|---|
| | | Fold-change | P-value | Fold-change | P-value |
| hsa-miR-106a | 100 | 20.2 | 1.33E−21 | 4.37 | 3.36E−07 |
| hsa-miR-17 | 95.6 | 17.9 | 5.62E−08 | 1.35 | 0.418 |
| hsa-miR-20a | 91.3 | 21.8 | 2.86E−07 | 1.34 | 0.583 |
| hsa-miR-93 | 78.3 | 8.9 | 1.63E−06 | 3.72 | 0.000126 |
| hsa-miR-18a | 73.9 | 12.9 | 1.81E−07 | 3.69 | 0.00351 |
| hsa-miR-18b | 73.9 | 15.7 | 2.29E−20 | 4.73 | 1.19E−05 |
| hsa-miR-29b | 100 | 6.39 | 3.32E−16 | 2.78 | 7.02E−09 |
| hsa-miR-29c | 86.4 | 5.62 | 6.43E−18 | 2.82 | 1.18E−11 |

TABLE 4-continued

Normalized miR expressionas measured by RT-PCR in similar sequences

| miR name | Carcinoid vs Squamous | | Small vs NonSquamous | |
|---|---|---|---|---|
| | Fold-change | P-value | Fold-change | P-value |
| hsa-miR-106a | 4.84 | 4.69E−14 | 4.63 | 9.87E−08 |
| hsa-miR-17 | 3.31 | 0.00281 | 13.2 | 1.16E−05 |
| hsa-miR-20a | 3.32 | 0.00482 | 16.3 | 5.97E−05 |
| hsa-miR-93 | 7.99 | 3.28E−06 | 2.39 | 0.000499 |
| hsa-miR-18a | 7.11 | 1.01E−05 | 3.51 | 0.0031 |
| hsa-miR-18b | 5.49 | 6.39E−16 | 3.31 | 0.000461 |
| hsa-miR-29b | 2.69 | 2.71E−10 | 2.3 | 4.97E−06 |
| hsa-miR-29c | 2.67 | 3.60E−14 | 1.99 | 1.58E−05 |

| miR name | Small vs Squamous | | NonSquamous vs Squamous | |
|---|---|---|---|---|
| | Fold-change | P-value | Fold-change | P-value |
| hsa-miR-106a | 4.17 | 1.47E−08 | 1.11 | 0.155 |
| hsa-miR-17 | 5.39 | 0.00268 | 2.45 | 0.0431 |
| hsa-miR-20a | 6.56 | 0.00401 | 2.48 | 0.0576 |
| hsa-miR-93 | 1.11 | 0.067 | 2.15 | 0.00651 |
| hsa-miR-18a | 1.82 | 0.124 | 1.93 | 0.0786 |
| hsa-miR-18b | 2.86 | 5.83E−05 | 1.16 | 0.192 |
| hsa-miR-29b | 2.38 | 1.21E−06 | 1.04 | 0.982 |
| hsa-miR-29c | 2.11 | 1.07E−06 | 1.06 | 0.958 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method for classifying a lung cancer as a subtype selected from the group consisting of squamous cell carcinoma, non-squamous non-small cell lung cancer (NSCLC), carcinoid lung cancer, and small cell lung carcinoma, the method comprising: providing RNA obtained from a lung cancer sample from a human subject in need thereof; determining an expression profile of nucleic acid sequences comprising SEQ ID NOS: 1-8 in said lung cancer sample, wherein the expression profile is determined by nucleic acid amplification comprising contacting the RNA of said lung cancer sample with forward primers comprising SEQ ID NOs: ii and 12; using a classifier algorithm to compare said expression profile to a training data set comprising expression levels of SEQ ID NOs: 1-8 determined in diagnosed lung cancers from each of said lung cancer subtype; wherein the comparison of said expression profile to said training data set assigns said lung cancer sample to one of said subtypes of lung cancer; and classifying said lung cancer sample into one of said subtypes based on said comparison.

2. The method of claim 1, wherein relatively high expression levels of SEQ ID NOS: 3, 7, and 8 as compared to said training data set, is indicative of carcinoid lung cancer.

3. The method of claim 1, wherein relatively high expression levels of SEQ ID NO: 1 as compared to said training data set, is indicative of small cell lung cancer (SCLC).

4. The method of claim 1, wherein relatively high expression levels of SEQ ID NOS: 2, 5, and 6 as compared to said training data set, is indicative of non-squamous non-small cell lung cancer (NSCLC).

5. The method of claim 1, wherein relatively high expression levels of SEQ ID NO: 4 as compared to said training data set, is indicative of squamous cell carcinoma.

6. The method of claim 1, wherein said lung cancer sample is selected from the group consisting of bodily fluid and a tissue sample.

7. The method of claim 6, wherein said tissue is a fresh, frozen, fixed, wax-embedded or formalin fixed paraffin-embedded (FFPE) tissue.

8. The method of claim 1, wherein the nucleic acid amplification method is real-time PCR.

9. The method of claim 8, wherein the real-time PCR method further comprises reverse primers.

10. The method of claim 9, wherein the forward primers further comprise a sequence selected from the group consisting of SEQ ID NOS: 9, 10, and 13-16.

11. The method of claim 10, wherein the real-time PCR method comprises at least one probe.

12. The method of claim 11, wherein the probe comprises a sequence selected from the group consisting of any one of SEQ ID NOS: 17-24.

13. The method of claim 1, wherein the classifier algorithm is K-nearest neighbor.

* * * * *

SEQUENCE LISTING

```
<160> NUMBER OF SEQ ID NOS: 61

<210> SEQ ID NO 1
<211> LENGTH: 23
<212> TYPE: RNA
<213> ORGANISM: Homo sapiens

<400> SEQUENCE: 1
aaaagugcuu acagugcagg uag                                           23

<210> SEQ ID NO 2
<211> LENGTH: 24
<212> TYPE: RNA
<213> ORGANISM: Homo sapiens

<400> SEQUENCE: 2
ucccugagac ccuuuaaccu guga                                          24

<210> SEQ ID NO 3
<211> LENGTH: 22
<212> TYPE: RNA
<213> ORGANISM: Homo sapiens

<400> SEQUENCE: 3
```
aagcccuuac cccaaaaagc au          22

<210> SEQ ID NO 4
<211> LENGTH: 22
<212> TYPE: RNA
<213> ORGANISM: Homo sapiens

<400> SEQUENCE: 4
uccuucauuc caccggaguc ug          22

<210> SEQ ID NO 5
<211> LENGTH: 22
<212> TYPE: RNA
<213> ORGANISM: Homo sapiens

<400> SEQUENCE: 5
uagcuuauca gacugauguu ga          22

<210> SEQ ID NO 6
<211> LENGTH: 23
<212> TYPE: RNA
<213> ORGANISM: Homo sapiens

<400> SEQUENCE: 6
uagcaccauu ugaaaucagu guu         23

<210> SEQ ID NO 7
<211> LENGTH: 22
<212> TYPE: RNA
<213> ORGANISM: Homo sapiens

<400> SEQUENCE: 7
uuuguucguu cggcucgcgu ga          22

<210> SEQ ID NO 8
<211> LENGTH: 23
<212> TYPE: RNA
<213> ORGANISM: Homo sapiens

<400> SEQUENCE: 8
uggaagacua gugauuuugu ugu         23

<210> SEQ ID NO 9
<211> LENGTH: 29
<212> TYPE: DNA
<213> ORGANISM: Artificial sequence
<220> FEATURE:
<223> OTHER INFORMATION: Synthetic

<400> SEQUENCE: 9
cagtcatttg gaaaagtgct tacagtgca   29

<210> SEQ ID NO 10
<211> LENGTH: 24
<212> TYPE: DNA
<213> ORGANISM: Artificial sequence
<220> FEATURE:
<223> OTHER INFORMATION: Synthetic

<400> SEQUENCE: 10
gctccctgag acccttttaac ctgt       24

<210> SEQ ID NO 11
<211> LENGTH: 24

```
<212> TYPE: DNA
<213> ORGANISM: Artificial sequence
<220> FEATURE:
<223> OTHER INFORMATION: Synthetic

<400> SEQUENCE: 11
gcaagccctt accccaaaaa gcat                                              24

<210> SEQ ID NO 12
<211> LENGTH: 29
<212> TYPE: DNA
<213> ORGANISM: Artificial sequence
<220> FEATURE:
<223> OTHER INFORMATION: Synthetic

<400> SEQUENCE: 12
cagtcatttg gctccttcat tccaccgga                                         29

<210> SEQ ID NO 13
<211> LENGTH: 28
<212> TYPE: DNA
<213> ORGANISM: Artificial sequence
<220> FEATURE:
<223> OTHER INFORMATION: Synthetic

<400> SEQUENCE: 13
cagtcatttg gctagcttat cagactga                                          28

<210> SEQ ID NO 14
<211> LENGTH: 30
<212> TYPE: DNA
<213> ORGANISM: Artificial sequence
<220> FEATURE:
<223> OTHER INFORMATION: Synthetic

<400> SEQUENCE: 14
catttggtag caccatttga aatcagtgtt                                        30

<210> SEQ ID NO 15
<211> LENGTH: 28
<212> TYPE: DNA
<213> ORGANISM: Artificial sequence
<220> FEATURE:
<223> OTHER INFORMATION: Synthetic

<400> SEQUENCE: 15
cagtcatttg ggtttgttcg ttcggctc                                          28

<210> SEQ ID NO 16
<211> LENGTH: 28
<212> TYPE: DNA
<213> ORGANISM: Artificial sequence
<220> FEATURE:
<223> OTHER INFORMATION: Synthetic

<400> SEQUENCE: 16
cagtcatttg gctggaagac tagtgatt                                          28

<210> SEQ ID NO 17
<211> LENGTH: 23
<212> TYPE: DNA
<213> ORGANISM: Artificial sequence
<220> FEATURE:
<223> OTHER INFORMATION: Synthetic

<400> SEQUENCE: 17
```
ccgttttttt tttttctacc tgc                                           23

<210> SEQ ID NO 18
<211> LENGTH: 18
<212> TYPE: DNA
<213> ORGANISM: Artificial sequence
<220> FEATURE:
<223> OTHER INFORMATION: Synthetic

<400> SEQUENCE: 18
aaaaccgata gtgagtcg                                                 18

<210> SEQ ID NO 19
<211> LENGTH: 18
<212> TYPE: DNA
<213> ORGANISM: Artificial sequence
<220> FEATURE:
<223> OTHER INFORMATION: Synthetic

<400> SEQUENCE: 19
aaaaccgata gtgagtcg                                                 18

<210> SEQ ID NO 20
<211> LENGTH: 22
<212> TYPE: DNA
<213> ORGANISM: Artificial sequence
<220> FEATURE:
<223> OTHER INFORMATION: Synthetic

<400> SEQUENCE: 20
cgtttttttt ttttcagact cc                                            22

<210> SEQ ID NO 21
<211> LENGTH: 23
<212> TYPE: DNA
<213> ORGANISM: Artificial sequence
<220> FEATURE:
<223> OTHER INFORMATION: Synthetic

<400> SEQUENCE: 21
ccgttttttt tttttcaaca tca                                           23

<210> SEQ ID NO 22
<211> LENGTH: 18
<212> TYPE: DNA
<213> ORGANISM: Artificial sequence
<220> FEATURE:
<223> OTHER INFORMATION: Synthetic

<400> SEQUENCE: 22
aaaaccgata gtgagtcg                                                 18

<210> SEQ ID NO 23
<211> LENGTH: 23
<212> TYPE: DNA
<213> ORGANISM: Artificial sequence
<220> FEATURE:
<223> OTHER INFORMATION: Synthetic

<400> SEQUENCE: 23
ccgttttttt tttttcacgc gag                                           23

<210> SEQ ID NO 24
<211> LENGTH: 23
<212> TYPE: DNA
<213> ORGANISM: Artificial sequence

```
<220> FEATURE:
<223> OTHER INFORMATION: Synthetic

<400> SEQUENCE: 24 ccgtttttt ttttttacaac aaa                                              23

<210> SEQ ID NO 25
<211> LENGTH: 22
<212> TYPE: DNA
<213> ORGANISM: Artificial sequence
<220> FEATURE:
<223> OTHER INFORMATION: Synthetic

<400> SEQUENCE: 25
gcgagcacag aattaatacg ac                                               22

<210> SEQ ID NO 26
<211> LENGTH: 81
<212> TYPE: RNA
<213> ORGANISM: Homo sapiens

<400> SEQUENCE: 26
ccuuggccau guaaaagugc uuacagugca gguagcuuuu ugagaucuac ugcaauguaa      60
gcacuucuua cauuaccaug g                                                81

<210> SEQ ID NO 27
<211> LENGTH: 86
<212> TYPE: RNA
<213> ORGANISM: Homo sapiens

<400> SEQUENCE: 27
ugccagucuc uagguccoug agacccuuua accugugagg acauccaggg ucacaggoga      60 gguucuuggg agccuggcgu cuggcc                                           86

<210> SEQ ID NO 28
<211> LENGTH: 72
<212> TYPE: RNA
<213> ORGANISM: Homo sapiens

<400> SEQUENCE: 28
ggaucuuuuu gcggucuggg cuugcuguuc cucucaacag uagucaggaa gcccuuaccc      60
caaaaaguau cu                                                          72

<210> SEQ ID NO 29
<211> LENGTH: 90
<212> TYPE: RNA
<213> ORGANISM: Homo sapiens

<400> SEQUENCE: 29
ugcccuucgc gaaucuuuuu gcggucuggg cuugcuguac auaacucaau agccggaagc      60 ccuuaccoca aaaagcauuu gcggagggcg                                       90

<210> SEQ ID NO 30
<211> LENGTH: 110
<212> TYPE: RNA
<213> ORGANISM: Homo sapiens

<400> SEQUENCE: 30
aaagauccuc agacaaucca ugugcuucuc uugccuuca uuccaccgga gucugucuca      60
uacccaacca gauuucagug gagugaaguu caggaggcau ggagcugaca               110
```

<210> SEQ ID NO 31
<211> LENGTH: 72
<212> TYPE: RNA
<213> ORGANISM: Homo sapiens

<400> SEQUENCE: 31
ugucggguag cuuaucagac ugauguugac uguugaaucu cauggcaaca ccagucgaug    60
ggcugucuga ca    72

<210> SEQ ID NO 32
<211> LENGTH: 81
<212> TYPE: RNA
<213> ORGANISM: Homo sapiens

<400> SEQUENCE: 32
cuucaggaag cugguuucau auggugguuu agauuuaaau agugauuguc uagcaccauu    60
ugaaaucagu guucuugggg g    81

<210> SEQ ID NO 33
<211> LENGTH: 81
<212> TYPE: RNA
<213> ORGANISM: Homo sapiens

<400> SEQUENCE: 33
cuucuggaag cugguuucac aughugggcuu agauuuuucc aucuuuguau cuagcaccau    60
uugaaaucag uguuuuagga g    81

<210> SEQ ID NO 34
<211> LENGTH: 64
<212> TYPE: RNA
<213> ORGANISM: Homo sapiens

<400> SEQUENCE: 34
ccccgcgacg agccccucgc acaaaccgga ccugagcguu uguucguuc ggcucgcgug    60 aggc    64

<210> SEQ ID NO 35
<211> LENGTH: 110
<212> TYPE: RNA
<213> ORGANISM: Homo sapiens

<400> SEQUENCE: 35
uuggauguug gccuaguucu guguggaaga cuagugauuu uguuguuuuu agauaacuaa    60
aucgacaaca aaucacaguc ugccauaugg cacaggccau gccucuacag    110

<210> SEQ ID NO 36
<211> LENGTH: 110
<212> TYPE: RNA
<213> ORGANISM: Homo sapiens

<400> SEQUENCE: 36
cuggauacag aguggaccgg cuggccccau cuggaagacu agugauuuug uuguugucuu    60
acugcgcuca caacaaauc ccagucuacc uaauggugcc agccaucgca    110

<210> SEQ ID NO 37
<211> LENGTH: 110
<212> TYPE: RNA
<213> ORGANISM: Homo sapiens

<400> SEQUENCE: 37

-continued agauuagagu ggcugugguc uagugcugug uggaagacua gugauuugu uguucugaug    60 uacuacgaca acaagucaca gccggccuca uagcgcagac ucccuucgac             110

<210> SEQ ID NO 38
<211> LENGTH: 23
<212> TYPE: RNA
<213> ORGANISM: Homo sapiens

<400> SEQUENCE: 38
caaagugcuu acagugcagg uag                                          23

<210> SEQ ID NO 39
<211> LENGTH: 23
<212> TYPE: RNA
<213> ORGANISM: Homo sapiens

<400> SEQUENCE: 39
uaaagugcuu auagugcagg uag                                          23

<210> SEQ ID NO 40
<211> LENGTH: 23
<212> TYPE: RNA
<213> ORGANISM: Homo sapiens

<400> SEQUENCE: 40
caaagugcug uucgugcagg uag                                          23

<210> SEQ ID NO 41
<211> LENGTH: 23
<212> TYPE: RNA
<213> ORGANISM: Homo sapiens

<400> SEQUENCE: 41
uaaggugcau cuagugcaga uag                                          23

<210> SEQ ID NO 42
<211> LENGTH: 23
<212> TYPE: RNA
<213> ORGANISM: Homo sapiens

<400> SEQUENCE: 42
uaaggugcau cuagugcagu uag                                          23

<210> SEQ ID NO 43
<211> LENGTH: 84
<212> TYPE: RNA
<213> ORGANISM: Homo sapiens

<400> SEQUENCE: 43
gucagaauaa ugucaaagug cuuacagugc agguagugau augugcaucu acugcaguga    60
aggcacuugu agcauuaugg ugac                                          84

<210> SEQ ID NO 44
<211> LENGTH: 71
<212> TYPE: RNA
<213> ORGANISM: Homo sapiens

<400> SEQUENCE: 44
guagcacuaa agugcuuaua gugcagguag uguuuaguua ucuacugcau uaugagcacu    60
uaaaguacug c                                                        71

```
<210> SEQ ID NO 45
<211> LENGTH: 80
<212> TYPE: RNA
<213> ORGANISM: Homo sapiens

<400> SEQUENCE: 45 cuggggcuc caaagugcug uucgugcagg uagugugauu acccaaccua cugcugagcu      60
agcacuuccc gagccccgg                                                 80

<210> SEQ ID NO 46
<211> LENGTH: 71
<212> TYPE: RNA
<213> ORGANISM: Homo sapiens

<400> SEQUENCE: 46
uguucuaagg ugcaucuagu gcagauagug aaguagauua gcaucuacug cccuaagugc     60
uccuucuggc a                                                         71

<210> SEQ ID NO 47
<211> LENGTH: 71
<212> TYPE: RNA
<213> ORGANISM: Homo sapiens

<400> SEQUENCE: 47
uguguuaagg ugcaucuagu gcaguuagug aagcagcuua gaaucuacug cccuaaaugc     60
cccuucuggc a                                                         71

<210> SEQ ID NO 48
<211> LENGTH: 22
<212> TYPE: RNA
<213> ORGANISM: Homo sapiens

<400> SEQUENCE: 48
uagcaccauu ugaaaucggu ua                                             22

<210> SEQ ID NO 49
<211> LENGTH: 88
<212> TYPE: RNA
<213> ORGANISM: Homo sapiens

<400> SEQUENCE: 49
aucucuuaca caggcugacc gauuucuccu ggguucaga gucuguuuuu gcuagcacc       60 auuugaaauc gguuaugaug uaggggga                                       88

<210> SEQ ID NO 50
<211> LENGTH: 28
<212> TYPE: DNA
<213> ORGANISM: Artificial sequence
<220> FEATURE:
<223> OTHER INFORMATION: Synthetic

<400> SEQUENCE: 50
cagtcatttg gccaaagtgc ttacagtg                                       28

<210> SEQ ID NO 51
<211> LENGTH: 29
<212> TYPE: DNA
<213> ORGANISM: Artificial sequence
<220> FEATURE:
<223> OTHER INFORMATION: Synthetic

<400> SEQUENCE: 51
```
cagtcatttg gtaaagtgct tatagtgca                                29

<210> SEQ ID NO 52
<211> LENGTH: 28
<212> TYPE: DNA
<213> ORGANISM: Artificial sequence
<220> FEATURE:
<223> OTHER INFORMATION: Synthetic

<400> SEQUENCE: 52
cagtcatttg gccaaagtgc tgttcgtg                                 28

<210> SEQ ID NO 53
<211> LENGTH: 28
<212> TYPE: DNA
<213> ORGANISM: Artificial sequence
<220> FEATURE:
<223> OTHER INFORMATION: Synthetic

<400> SEQUENCE: 53
cagtcatttg gctaaggtgc atctagtg                                 28

<210> SEQ ID NO 54
<211> LENGTH: 28
<212> TYPE: DNA
<213> ORGANISM: Artificial sequence
<220> FEATURE:
<223> OTHER INFORMATION: Synthetic

<400> SEQUENCE: 54
cagtcatttg gctaaggtgc atctagtg                                 28

<210> SEQ ID NO 55
<211> LENGTH: 28
<212> TYPE: DNA
<213> ORGANISM: Artificial sequence
<220> FEATURE:
<223> OTHER INFORMATION: Synthetic

<400> SEQUENCE: 55
cagtcatttg gctagcacca tttgaaat                                 28

<210> SEQ ID NO 56
<211> LENGTH: 23
<212> TYPE: DNA
<213> ORGANISM: Artificial sequence
<220> FEATURE:
<223> OTHER INFORMATION: Synthetic

<400> SEQUENCE: 56 ccgtttttttt tttttctacc tgc                                    23

<210> SEQ ID NO 57
<211> LENGTH: 23
<212> TYPE: DNA
<213> ORGANISM: Artificial sequence
<220> FEATURE:
<223> OTHER INFORMATION: Synthetic

<400> SEQUENCE: 57 ccgtttttttt tttttctacc tgc                                    23

<210> SEQ ID NO 58
<211> LENGTH: 23
<212> TYPE: DNA

```
<213> ORGANISM: Artificial sequence
<220> FEATURE:
<223> OTHER INFORMATION: Synthetic

<400> SEQUENCE: 58 ccgtttttt tttttctacc tgc                                              23

<210> SEQ ID NO 59
<211> LENGTH: 23
<212> TYPE: DNA
<213> ORGANISM: Artificial sequence
<220> FEATURE:
<223> OTHER INFORMATION: Synthetic

<400> SEQUENCE: 59 ccgtttttt tttttctatc tgc                                              23

<210> SEQ ID NO 60
<211> LENGTH: 23
<212> TYPE: DNA
<213> ORGANISM: Artificial sequence
<220> FEATURE:
<223> OTHER INFORMATION: Synthetic

<400> SEQUENCE: 60 ccgtttttt tttttctaac tgc                                              23

<210> SEQ ID NO 61
<211> LENGTH: 23
<212> TYPE: DNA
<213> ORGANISM: Artificial sequence
<220> FEATURE:
<223> OTHER INFORMATION: Synthetic

<400> SEQUENCE: 61 ccgtttttt ttttaaccg att                                               23
```